United States Patent [19]
Olsson et al.

[11] Patent Number: 5,952,293
[45] Date of Patent: Sep. 14, 1999

[54] RECEPTOR DERIVED PEPTIDES INVOLVED IN INHIBITION OF RECEPTOR INTERNALIZATION IN RESPONSE TO LIGAND BINDING

[75] Inventors: Lennart Olsson, Orinda; Tatajna Navrenda, Mountain View, both of Calif.

[73] Assignee: Receptron, Mountain View, Calif.

[21] Appl. No.: 08/612,999

[22] Filed: Mar. 8, 1996

[51] Int. Cl.$^6$ .......................... A61K 38/04; A61K 38/16; C07K 14/705; C07K 14/74

[52] U.S. Cl. ..................................... 514/2; 514/8; 514/12; 514/13; 514/14; 514/15; 514/16; 435/7.21; 530/300; 530/324; 530/325; 530/326; 530/327; 530/328; 530/350

[58] Field of Search .................................... 530/300, 303, 530/387.1, 388.2, 388.22, 350, 324–328; 514/2, 3, 8, 12–16; 435/69.1, 240.2, 4, 7.1, 325, 7.21

[56] References Cited

U.S. PATENT DOCUMENTS 5,385,888   1/1995   Goodenow et al. ....................... 514/12

FOREIGN PATENT DOCUMENTS

90/10016   9/1990   WIPO .
95/05189   2/1995   WIPO .

OTHER PUBLICATIONS

Korpi et al., Natural mutation of GABAA receptor alpha6 subunit alters benzodiazepine affinity but not allosteric GABA effects, Eur. J. Pharm., 247:23–27, 1993.

Strader et al., Structrual basis of beta–adrenergic receptor function, FASEB J., 3:1825–1832, 1989.

Rudinger, Characteristics of the amino acids as components of a peptide hormone sequence, In Peptide Hormones, J. Parsons, Ed., University Park Press:Baltimore, MD, pp. 1–6, Jun. 1976.

Tyndale et al., GABAA receptors, In Handbook of Receptors and Channels, S. Peroutka, Ed., CRC Press:USA, pp. 265–291, Nov. 1994.

"Specific Molecular Interaction Between The Insulin Receptor and a D Product of MHC Class 1", Sten Verland, Morten Simonsen, Steen Gammeltoft, Hamish Allen, Richard A. Flavell, Lennart Olsson, The Journal of Immunology, 1989, pp. 945–951.

"Correlation between Insulin Receptor Occupany and Tyrosine Kinase Activity at Low Insulin Concentrations and Effect of Major Histocompatibility Complex Class I–Derived Peptide", Jan Stagsted, Torben Hansen, Richard A. Roth, Avram Goldstein, and Lennart Olsson, The Journal of Pharmacology and Experimental Therapeutics, 1993, pp. 997–1001.

A Preformed, Ordered Structure of a 25–residue Peptide Derived from a Major Histocompatibility Complex Class I Antigen Is Required to Affect Insulin Receptor Function, Jan Stagsted, Walter A. Basse, Avram Goldstein, Lennart Olsson, The Journal of Biological Chemistry, 1991, pp. 12844–12847.

"Chimeric Receptors Expressing Juxtamembrane Sequences of the Insulin Receptor Undergo Rapid Endocytosis in the Absence of Receptor Tyrosine Kinase Activity",Malini Rajagopalan, Lee Hebert, Donald A. McClain, Biochemical and Biophysical Research Communications, Jun. 26, 1995, pp. 714–718.

"Deletion of C–terminal 113 amino acids impairs processing and internalization of human insulin receptor: comparison of receptors expressed in CHO and NIH–3T3 cells", Rachel Levy–Toledano, Domenico Accili and Simeon I. Taylor, 1993 Elsevier Science Publishers B.V., pp. 1–14.

"Localization of the Insulin Receptor Binding Sites for the SH2 Domain Proteins p85, Syp, and GAP", Patricia A. Staubs, Donna R. Reichart, Alan R. Saltiel, Kim L. Milarski, Hiroshi Maegawa, Paulos Berhanu, Jerrold M. Olefsky, B. Lynn Seely, The Journal of Biological Chemistry, Nov. 4, 1994, pp. 27186–27192.

"Regulation of Insulin Receptor Functions by a Peptide Erived from a Major Histocompatibility Complex Class I Antigen", Jan Stagsted, Gerald M. Reaven, Torben Hansen, Avram Goldstein, Lennart Olsson, Cell, vol. 62, Jul. 27, 1990, pp. 297–307.

"An Irregularity in the Transmembrane Domain Helix Correlates with the Rate of Insulin Receptor Internalization", Shung–Cheng Li, Charles M. Deber, Steven E. Shoelson, Biochemistry 1994, pp. 14333–14338.

Distinct Signals in the GLUT4 Glucose Transporter for Internalization and for Targeting to an Insulin–responsive Compartment, Kristen J. Verhey, Jih–I Yeh, and Morris J. Birnbaum, The Journal of Cell Biology, vol. 130, No. 5, Sep. 1995, pp. 1071–1079.

Inhibition of insulin receptor phosphorylation by peptides derived from major histocompatibility complex class I antigens, Torben Hansen, Jan Stagsted, Lars Pedersen, Richard A. Roth, Avram Goldstein, Lennart Olsson, Proc, Natl. Acad. Sci, USA vol. 86, pp. 3123–3126, May 1989.

(List continued on next page.)

*Primary Examiner*—Lila Feisee
*Assistant Examiner*—Claire M. Kaufman
*Attorney, Agent, or Firm*—Flehr Hohbach Test Albritton & Herbert LLP

[57] ABSTRACT

Oligopeptides having an amino acid sequence corresponding to a receptor's extracellular domain, and having sequence similarity to regulatory peptides from MHC class I antigens, enhance the physiological response of ligand binding to the corresponding receptor. The oligopeptides are used in diagnosis and therapy of diseases that involve inadequate or inappropriate receptor response as well as in the screening of drug candidates that affect surface expression of receptors. Also useful for drug screening is a modified receptor molecule, where the sequence corresponding to the regulatory peptide is modified or deleted.

6 Claims, No Drawings

OTHER PUBLICATIONS

Piper et al., The efficient intracellular sequestration of the insulin–regulatable glucose transporter (GLUT–4) is conferred by the NH2 terminus, J. Cell Biol., 117(4): 729–743, May 1992.

GenBank Accession No. D28561, accessed Apr. 13, 1998, Sep. 1994.

Olsson et al., Regulation of receptor internalization by the major histocompatibility complex class I molecule, Proc, Natl. Acad. Sci. USA, 91: 9086–9090, Sep. 1994.

Stagsted et al., Inhibition of internalization of glucose tranmsporter and IGF–II receptors, J. Biol. Chem., 268(30):22809–22813, Oct. 1993.

RECEPTOR DERIVED PEPTIDES INVOLVED IN INHIBITION OF RECEPTOR INTERNALIZATION IN RESPONSE TO LIGAND BINDING

TECHNICAL FIELD

The field of this invention is peptides involved in the modulation of response to ligands by cell surface receptors.

BACKGROUND

The complex regulatory balance between hormones, receptors and responding cells is critical to the correct functioning of multicellular organisms. Subtle environmental and genetic factors can disrupt this balance, sometimes resulting in disease. The advent of molecular biology has meant that medically important hormones can be made available in therapeutically useful amounts. Among them are human growth hormone, insulin-like growth factor, insulin, epidermal growth factor, and numerous others.

A condition of great economic and medical significance is insulin resistance, which is an essential feature of a great variety of clinical disorders, such as diabetes mellitus, obesity and certain types of hypertension. Individuals with non-insulin dependent diabetes present with insulin resistance in peripheral tissues. They have a subnormal glucose utilization in skeletal muscle, where glucose transport across the cell membrane of skeletal muscle is the rate limiting step in glucose metabolism. It is possible that a defect exists in insulin-dependent glucose transport in skeletal muscle in diabetic states, where decreased levels of the glucose transporter 4 protein (GLUT4) have been observed. In adipose and muscle cells, insulin stimulates a rapid and dramatic increase in glucose uptake, primarily by promoting the redistribution of the GLUT4 glucose transporter from its intracellular storage site to the plasma membrane.

Insulin resistance may also be attributed to a defect in insulin action at the cellular level. The insulin receptor is activated by binding of insulin to the alpha-subunit of the receptor, which causes autophosphorylation of the intracellular beta-subunit region. The activated insulin receptor couples to cytosolic receptor substrates that can affect signaling cascades, resulting in the pleiotropic hormone response. Most proteins involved in the signal transduction pathway are not known yet, but each of them might play a role in the various forms of insulin resistance. The heterogeneous nature of insulin resistance makes treatments that can act "upstream" of the signal transduction pathways very attractive, because a number of different pathologies could be treated with a single drug.

Specific peptides have been previously shown to enhance the cellular response to certain hormones. This effect has been attributed to inhibition of the internalization of the corresponding hormone receptors. Insulin-stimulated glucose uptake is increased by adding the peptides to responding cells, offering the possibility of improved therapy for insulin dependent and insulin resistant diabetes. The enhanced response may also be exploited in therapies involving other hormones. Improvements in the specificity of agents that enhance the activity of insulin and other hormones are of considerable interest for their therapeutic benefits. The site of action for such peptides on receptors molecules is of interest for drug evaluation and design.

RELEVANT LITERATURE

Several groups have examined the glucose transporter and insulin receptor for residues that are involved in internalization. Rajagopalan et al. (1995) *Biochem Biophys Res Commun* 211:714–8 found that residues GPYL950–953 served as the predominant endocytosis signal and the sequence NPEY957–960 as a secondary signal. Levy-Toledano et al. (1993) *Biochim Biophys Acta* 1220:1–14 suggest that the structural domain located 43–113 amino acids from the C-terminus is required in intact cells for insulin-stimulated autophosphorylation and signal transmission. Verhey et al. (1995) *J Cell Biol* 130:1071–9 identified sequences involved in the differential subcellular localization and hormone-responsiveness of glucose transporter isoforms. The COOH-terminal 30 amino acids of GLUT4 are sufficient for its correct localization to an intracellular storage pool that translocates to the cell surface in response to insulin.

U.S. Pat. No. 5,385,888, issued Jan. 31, 1995, describes Class I MHC peptide modulation of surface receptor activity. Data presented in International patent application PCT/US94/09189 suggest that these peptides must be in an ordered conformation to be biologically active. The composition and uses of such peptides are further described in International application PCT/US93/01758. The peptides are further disclosed in International application PCT/US89/00876.

Regulation of receptor internalization by the major histocompatibility complex class I molecule is shown by Olsson et al. (1994) i *Proc Natl Acad Sci* 91:9086–90. Peptides derived from the alpha 1 domain of the major histocompatibility complex class I protein (MHC-I) inhibit internalization of some receptors, thereby increasing the steady-state number of active receptors on the cell surface. It is suggested that MHC-I participates in the regulation of cell surface receptor activity. Stagsted et al. (1993) *J Biol Chem* 268:22809–13 demonstrate that such peptides inhibit the internalization of glucose transporters (GLUT4) and insulin-like growth factor II (IGF-II) receptors in insulin-stimulated cells.

SUMMARY OF THE INVENTION

Methods and compositions are provided for modulating the response of cell surface receptors to ligand binding, by administration of oligopeptides having at least substantially the amino acid sequence of a portion of that receptor's extracellular domain. The receptor derived peptides have sequence similarity to previously described regulatory peptides from the major histocompatibility complex class I antigens. The methods and compositions of the subject invention are used in diagnosis and therapy of diseases that involve inadequate or inappropriate receptor response as well as in the screening of drug candidates that may affect surface expression of receptors. Also useful for drug screening is a modified receptor molecule, where the sequence corresponding to the regulatory peptide is modified or deleted.

DATABASE REFERENCES FOR NUCLEOTIDE AND AMINO ACID SEQUENCES

The complete mRNA sequence encoding the human insulin responsive glucose transporter (GLUT4) has the Genbank accession number M20747, published by Fukumoto et al. (1989) *J. Biol. Chem.* 264:7776–7779. The complete mRNA sequence encoding the human insulin receptor has the Genbank accession number A18657, published in International Patent Application no. WO/91/17253.

DESCRIPTION OF THE SPECIFIC EMBODIMENTS

Oligopeptides are provided that have an amino acid sequence at least substantially identical to the sequence of a portion of a cell surface receptor extracellular domain, and have sequence similarity to bioactive oligopeptides of the major histocompatibility locus class I antigens. The oligopeptides modulate the effect of ligand binding to the corresponding receptor, enhancing the physiological effect of the ligand. Receptors having a modification or deletion in this region are deficient in internalization, and are useful in drug screening assays.

Methods are provided for enhancing the physiological effect of ligand binding to cell surface receptors by administration of such bioactive, receptor-derived oligopeptides. The methods are used in diagnosis and therapy of diseases that involve inadequate or inappropriate receptor response, as well as in the screening of drug candidates that affect surface localization of receptors. Also useful for drug screening is a modified receptor molecule, where the sequence corresponding to the regulatory peptide is modified or deleted. The data suggest that internalization of the receptor is inhibited by the presence of the subject oligopeptides, thereby providing for a greater number of receptors on the cell surface, and increased effectiveness of ligand binding.

Receptors of interest are internalized or are recycled into the cytoplasm in response to ligand binding, e.g. insulin, insulin-like growth factor, human growth hormone, glucose transporters, transferrin, epidermal growth factor, low density lipoprotein, epidermal growth factor, etc. Receptors of particular interest are the insulin receptor and insulin sensitive glucose transporter. Generally, the regulatory peptide is derived from the sequence of the receptor that will be modulated. The oligopeptide sequence corresponds to the region of the receptor on the extracellular surface. Sequences of receptors, and positioning of the receptors in the cell membrane are known in the art. Such information may be accessed through public databases, as previously cited.

The oligopeptide will comprise, as an active motif sequence, at least 8 amino acids, usually at least about 12 amino acids, more usually at least about 18 amino acids, and fewer than about 40 amino acids, more usually fewer than 30 amino acids. It is understood that up to about three substitutions or deletions may be made in the subject sequences, where the change will not be more than about 20%, usually not more than about 10%, of the number of amino acids in the active motif. The oligopeptide may also be used as a dimer, generally as a head to tail dimer, where a spacer of from 1 to 3 small neutral amino acids may be present between the two active peptide sequences.

The active motif sequence has sequence similarity to the MHC derived peptide ERETQIAKGNEQSFRVDLRTLLR, (SEQ ID NO:1; U.S. Pat. No. 5,385,888, incorporated herein by reference), where there is at least about 20% sequence identity, usually at least about 30% sequence identity, and having at least about 30% sequence similarity, usually at least about 50% sequence similarity. Algorithms for sequence analysis are known in the art, and include BLAST, described in Altschul et al. (1990) *J Mol Biol* 215:403–10; ADVANCE and ADAM, described in Torelli and Robotti (1994) *Comput Appl Biosci* 10:3–5; and FASTA, described in Pearson and Lipman (1988) *P.N.A.S.* 85:2444–8. The sequence similarity was determined using the Wisconsin Package, version 8.0-OpenVMS, Genetics Computer Group.

In a preferred embodiment, the sequence is at least 12 amino acids, and is contained within the following amino acid sequences (SEQ ID NO:2): TWLGRQGPEGPSSIP-PGTLTTLW (glucose transporter, GLUT4) and (SEQ ID NO:3) KTDSQILKELEESSFRKTFEDYLH (insulin receptor). The oligopeptide may be modified from these sequences by amino acid substitutions, deletions and additions. Generally not more than three amino acids will be modified. Preferred are conservative substitutions, as known in the art, including substitutions within the large hydrophobic group: isoleucine, leucine, valine and phenylalanine; between serine and threonine; glycine and alanine; asparagine and glutamine; aspartic acid and glutamic acid; or lysine, arginine and histidine.

The oligopeptides of this invention may be prepared in accordance with conventional techniques, such as synthesis (for example, use of a Beckman Model 990 peptide synthesizer or other commercial synthesizer). Peptides may be produced directly by recombinant methods (see Sambrook et al. *Molecular Cloning: A Laboratory Manual*, CSHL Press, Cold Spring Harbor, N.Y., 1989) or as a fusion protein, for example to a protein that is one of a specific binding pair, allowing purification of the fusion protein by means of affinity reagents, followed by proteolytic cleavage, usually at a site engineered to yield the desired peptide (see for example Driscoll et al. (1993) *J. Mol. Bio.* 232:342–350).

The oligopeptides may be extended to provide convenient linking sites, e.g. cysteine or lysine, to enhance stability, to bind to particular receptors, to provide for site-directed action, to provide for ease of purification, to alter the physical characteristics (e.g. solubility, charge, etc.), to stabilize the conformation, etc. The oligopeptides may be joined to non-wild-type flanking regions as fused proteins, joined either by linking groups or covalently linked through cysteine (disulfide) or peptide linkages. The oligopeptide may be linked through a variety of bifunctional agents, such as maleimidobenzoic acid, methyldithioacetic acid, mercaptobenzoic acid, S-pyridyl dithiopropionate, etc. The oligopeptides may be joined to a single amino acid at the N- or C-terminus of a chain of amino acids, or may be internally joined. For example, the subject peptides may be covalently linked to an immunogenic protein, such as keyhole limpit hemacyanin, ovalbumin, etc. to facilitate antibody production to the subject oligopeptides.

Alternatively, the subject oligopeptides may be expressed in conjunction with other peptides or proteins, so as to be a portion of the chain, either internal, or at the N- or C-terminus. Various post-expression modifications may be achieved. For example, by employing the appropriate coding sequences, one may provide farnesylation or prenylation, such that the subject peptide will be bound to a lipid group at one terminus, and will be able to be inserted into a lipid membrane, such as a liposome.

The subject oligopeptides may be PEGylated, where the polyethyleneoxy group provides for enhanced lifetime in the blood stream. The subject oligopeptides may also be combined with other proteins, such as the Fc of an IgG isotype to enhance complement binding, or with a toxin, such as ricin, abrin, diphtheria toxin, or the like, particularly the A chain. The oligopeptides may be linked to antibodies for site directed action. For conjugation techniques, see, for example, U.S. Pat. Nos. 3,817,837; 3,853,914; 3,850,752; 3,905,654; 4,156,081; 4,069,105; and 4,043,989, which are incorporated herein by reference.

The subject oligopeptides act to enhance the cellular response to hormones that bind to the surface membrane receptor corresponding to the oligopeptide, e.g. insulin response is enhanced by the oligopeptide SEQ ID NO:3, glucose transport is enhanced by the oligopeptide SEQ ID NO:2, etc. Insulin, insulin-like growth factor, human growth hormone, glucose transporters, transferrin, epidermal growth factor, low density lipoprotein and epidermal growth factor are herein referred to as "therapeutic hormones". Enhancement of the cellular response to therapeutic hormones by the subject oligopeptides provides a means of improving the response of patients that are unresponsive, e.g. resistant, to the action of such hormones. The subject oligopeptides may be administered to patients requiring enhancement of the response to naturally occurring levels of the therapeutic hormone. Alternatively, the oligopeptides may be administered to patients in conjunction with a therapeutic hormone. Of particular interest is the treatment of insulin resistance, which may be associated with defects in glucose transport, or in the cellular response to insulin. Administration of the subject oligopeptides improves the response to insulin therapy.

For therapy, the oligopeptides may be administered topically or parenterally, e.g. by injection at a particular site, for example, subcutaneously, intraperitoneally, intravascularly, intranasally, transdermally or the like. Formulations for injection will comprise a physiologically-acceptable medium, such as water, saline, PBS, aqueous ethanol, aqueous ethylene glycols, or the like. Water soluble preservatives which may be employed include sodium bisulfite, sodium thiosulfate, ascorbate, benzalkonium chloride, chlorobutanol, thimerosal, phenylmercuric borate, parabens, benzyl alcohol and phenylethanol. These agents may be present in individual amounts of from about 0.001 to about 5% by weight and preferably about 0.01 to about 2%. Suitable water soluble buffering agents that may be employed are alkali or alkaline earth carbonates, phosphates, bicarbonates, citrates, borates, acetates, succinates and the like, such as sodium phosphate, citrate, borate, acetate, bicarbonate and carbonate. Additives such as carboxymethylcellulose may be used as a carrier in amounts of from about 0.01 to about 5% by weight. The formulation will vary depending upon the purpose of the formulation, the particular mode employed for modulating the receptor activity, the intended treatment, and the like. The formulation may involve patches, capsules, liposomes, time delayed coatings, pills, or may be formulated in pumps for continuous administration. The specific dosage can be determined empirically in accordance with known ways. See, for example Harrison's, Principles of Internal Medicine, 11th ed. Braunwald et al. ed, McGraw Hill Book Co., New York, 1987.

Generally, a therapeutically effective dose of the subject oligopeptides will be in the range of about 0.005–10, more usually from about 0.01–1 mg/kg of host weight. Such a dose will be sufficient to enhance the action of the therapeutic hormone, usually by at least as much as 50%. Administration may be as often as daily; usually not more than one or more times daily, or as infrequent as weekly, depending upon the level of drug which is administered. The oligopeptides may be administered alone, or in combination with the therapeutic hormone. The hormone may be administered at a normally therapeutically effective dose, or the dose may be decreased by as much as 50%, usually by as much as 25%, to compensate for the oligopeptide enhancement. The host may be any mammal including domestic animals, pets, laboratory animals and primates, particularly humans. The amount will generally be adjusted depending upon the half life of the peptide, where dosages in the lower portion of the range may be employed where the peptide has an enhanced half life or is provided as a depot, such as a slow release composition comprising particles, introduced in a matrix which maintains the peptide over an extended period of time, e.g., a collagen matrix, use of a pump which continuously infuses the peptide over an extended period of time over a substantially continuous rate, or the like. Heller, *Biodegradable Polymers in Controlled Drug Delivery*, in: CRC Critical Reviews in Therapeutic Drug Carrier Systems, Vol. 1, CRC Press, Boca Raton, Fla., 1987, pp 39–90, describes encapsulation for controlled drug delivery, and Di Colo (1992) *Biomaterials* 13:850–856 describes controlled drug release from hydrophobic polymers.

The subject oligopeptides and modified receptors find use in a drug screening assays. In a modified form of the receptor, the sequence corresponding to the regulatory peptide contains a deletion, substitution or insertion, such that the ability of the receptor to internalize in response to ligand binding is altered. The modification may include a deletion or substitution of the complete oligopeptide sequence, or a portion thereof. Modifications on interest include scanning mutations, where single amino acid residues are modified by substitution with an aliphatic amino acid, e.g. serine, alanine, glycine, valine, etc.

Conveniently, the modification is performed using recombinant DNA technology. The DNA sequence encoding the desired receptor may be obtained from various sources, or may be obtained from a cDNA library using probes derived from publically available sequence information. Techniques for in vitro mutagenesis of cloned genes are known; methods for site specific mutagenesis can be found in Sambrook, et al. supra. pp.15.3–15.108; Weiner et al. (1993) *Gene* 126:35–41; Sayers et al. (1992) *Biotechniques* 13:592–6; Jones and Winistorfer (1992) *Biotechniques* 12:528–30; Barton et al. (1990) *Nucleic Acids Res* 18:7349–55; Marotti and Tomich (1989) *Gene Anal Tech* 6:67–70 and Zhu (1989) *Anal Biochem* 177:120–4. For example, to delete a sequence, primers are devised that span the region. On hybridization, the region to be deleted forms a single stranded loop. The loop may be excised by nuclease digestion, or a suitable polymerase may be used to extend out from the primer.

For expression, the DNA sequences are inserted into an appropriate expression vector, where the native transcriptional initiation region may be employed or an exogenous transcriptional initiation region, i.e. a promoter other than the promoter which is associated with the gene in the normally occurring chromosome. The promoter may be introduced by recombinant methods in vitro, or as the result of homologous integration of the sequence into a chromosome. A wide variety of transcriptional initiation regions are known for a wide variety of expression hosts, where the expression hosts may involve prokaryotes or eukaryotes, particularly *E. coli; B. subtilis*; yeast cells; mammalian cells; e.g. Cos cells, HeLa cells, L(tk-), primary cultures; insect cells; *Xenopus laevis* oocytes; and the like. Generally a selectable marker operative in the expression host will be present. The promoter may be operably linked to the coding sequence of the genes of interest so as to produce a translatable mRNA transcript. Expression vectors have convenient restriction sites located near the promoter sequence so as to provide for the insertion of nucleic acid sequences encoding heterologous proteins. The promoters in suitable expression vectors may be either constitutive or inducible. Expression vectors for the production of fusion proteins, where the exogenous fusion peptide provides additional functionality, i.e. increased protein synthesis, stability, reactivity with defined antisera, an enzyme marker, e.g. β-galactosidase, etc.

Drug candidates capable of inhibiting surface receptor internalization are identified by first screening the drug candidates for the ability to compete with a peptide for association with a receptor, a saturable cell-surface binding site, or an accessory molecule(s) involved in surface receptor internalization, or for an effect on hormone responsiveness of a cell. Alternatively, differential screening may be performed to identify drug candidates that bind to the native receptor, but cannot bind to the subject modified receptors. Drug candidates that affect receptor internalization are also identified by screening drugs for the ability to either enhance or reduce the effect of peptides on the internalization of a selected surface receptor. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like.

The term "agent" as used herein describes any molecule, e.g. protein, oligopeptide, small organic molecule, polysaccharide, polynucleotide, etc. with the capability of directly or indirectly altering cell surface receptor internalization in response to ligand binding. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Where the screening assay is a binding assay, one or more of the molecules may be joined to a label, where the label can directly or indirectly provide a detectable signal. Various labels include radioisotopes, fluorescers, chemiluminescers, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule which provides for detection, in accordance with known procedures.

A variety of other reagents may be included in the screening assay. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc. may be used.

The mixture of components may be added in any order that provides for the requisite binding. Incubations may be performed at any temperature which facilitates optimal activity, typically between 4 and 40° C. Incubation periods are selected for optimum activity, but may also be optimized to facilitate rapid high-throughput screening. Typically between 0.1 and 1 hour will be sufficient.

The compounds having the desired pharmacological activity may be administered in a physiologically acceptable carrier to a host, as previously described. The inhibitory agents may be administered in a variety of ways, orally, parenterally e.g. subcutaneously, intraperitoneally, intravascularly, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

In one embodiment of the screening assay, a peptide having modulatory activity is non-diffusably bound to an insoluble support having isolated sample receiving areas (e.g. a microtiter plate). The insoluble supports may be made of any composition to which peptide, or receptor can be bound, is readily separated from soluble material, and is otherwise compatible with the overall method of screening. The surface of such supports may be solid or porous and of any convenient shape. Examples of suitable insoluble supports include microtiter plates, membranes and beads. These are typically made of glass, plastic (e.g. polystyrene), polysaccharides, nylon or nitrocellulose. Microtiter plates are especially convenient because a large number of assays can be carried out simultaneously, using small amounts of reagents and samples. The particular manner of binding of the peptide or other protein is not crucial so long as it is compatible with the reagents and overall methods of the invention, maintains the activity of the peptide and is nondiffusable. Following binding of the peptide, excess unbound material is removed by washing. The sample receiving areas may then be blocked through incubation with bovine serum albumin (BSA), casein or other innocuous protein.

The drug candidate and varying concentrations of the oligopeptide are added to each of the sample receiving areas containing support-bound peptide. The oligopeptide added is of substantially the same amino acid sequence as the oligopeptide bound to the support and is labeled. The oligopeptides could be labeled, directly or indirectly, with a label which provides a detectable signal, e.g. radioisotope, fluorescers, enzyme, particle, chemiluminescer, etc. Positive controls for binding of active peptide and competitive binding of active peptide may include samples containing labeled active peptide alone and a mixture of labeled active peptide and unlabeled active peptide, respectively. Samples containing labeled active peptide and unlabeled inactive peptide that does not aggregate with the bound peptide may serve as a negative control for competitive binding with peptide. Preferably all control and test samples are performed in at least triplicate to obtain statistically significant results. Incubation of all samples is for a time sufficient for the binding of the labeled active peptide to the support-bound peptide. Following incubation, all samples are washed free of non-specifically bound material and the amount of bound, labeled peptide determined. For example, where a radiolabel is employed in labeling the peptide, the samples may be counted in a scintillation counter to determine the amount of bound, labeled peptide.

In test samples containing the drug candidate, if the amount of labeled active peptide bound to the support-bound peptide or receptor is in the range of values of the positive control samples for competitive binding and is significantly less negative control samples for competitive binding, then the drug candidate in the test sample is able to successfully competitively bind the support-bound peptide. Drug candidates capable of such competitive binding may mediate modulation of cell surface expression of a receptor.

The following examples are offered by way of illustration and not by way of limitation.

EXPERIMENTAL

Methods

Insulin Receptor modification and expression. The human insulin receptor gene, as described in the database references and in Ebina et al. (1985) *Cell* 40:747–758) with a pCR3 expression vector (Invitrogen, catalog no. K3000-01) was transfected by electroporation into HeLa cells. Methods of electroporation are described in Boggs et al. (1986) *Ex. Hematol.* 149:988–994. In the transfected cells the receptors show insulin dependent internalization.

A mutated form of the insulin receptor was created by deleting residues 713 to 740 (SEQ ID NO:4; PKTDSQILKELEESSFRKTFEDYLHNV) using amplification primers that spanned the region to be deleted. The deletion mutant, mIR, was transfected into HeLa cells and internalization of the mIR was then tested.

Measurement of IR internalization. Receptor internalization was performed essentially as described in Stagsted et al. (1990) *Cell* 62:297–307. Briefly, 50 $\mu$l of the transfected cells at $10^6$ cells/ml were incubated in a shaking water bath at 37° C. with 625 pM $^{125}$I-labeled insulin in the absence or presence of 10 $\mu$M of peptide as shown in Table 1, and the final volume brought to 100 $\mu$l. The cells were then diluted with 50 $\mu$l of KRHB (pH7.2)(no acid wash) or 50 $\mu$l of KRHB (pH 2.0)(acid wash) and incubated on ice for 5 min. The cells were finally harvested by centrifugation on top of silicone oil, and both free and cell-associated radioactivity was measured.

Glucose Transport in Adipose Cells. The biological activity of the peptides were measured by their effect on glucose uptake in rat adipose cells as described (Stagsted et al. (1991) *J. Biol. Chem.* 266:12844–12847). Briefly, rat adipose cells were obtained from epididymal fat pads and suspended in Krebs-Ringer HEPES buffer (KRH) with 5% bovine serum albumin at a lipocrit of 10% (final). The peptide effect was measured in cells maximally stimulated with insulin (10 nM). After equilibration at 37° C. for 30 min the cells were incubated for 30 min at 37° C. with buffer (basal), 10 nM insulin plus peptide. $^{14}$C-D-glucose was added, and the cells were incubated for an additional 30 min and harvested on oil. Biological activity was measured by a dose-response curve to interpolate the $EC_{50}$ value, taking the maximum enhancement of insulin effect (about 40% over the insulin-only maximum) as 100%. Most of the peptides were not tested at higher concentrations than 30 $\mu$M. Peptides that enhanced the maximum insulin effect by less than 20% at 30 $\mu$M were considered inactive.

Peptides. The peptides were assembled stepwise either on a phenylacetamidomethyl (PAM) resin using the t-Boc NMP/HOBt protocol of an Applied Biosystems Model 430A peptide synthesizer, or on a p-alkoxy benzyl alcohol (Wang) resin using a modified Fmoc/BOP protocol of a Milligen/Biosearch Model 9600 synthesizer. The desired peptides were confirmed by sequence analysis, amino acid composition, and fast atom bombardment mass spectrometry. The peptides were activated by incubation of 1 mM stock solution at 37° C. in 0.1 M NaCl overnight (Stagsted et al. (1991) *J. Biol. Chem.* 266:12844–12847).

Results

Effect of peptides on receptor internalization. The kinetics of internalization for insulin receptor and mutated insulin receptor were determined in the absence or presence of the peptides: SEQ ID NO:3, KTDSQILKELEESSFRKTFEDYLH (pepIR) and SEQ ID NO:5, GNEQSFRVDLRTLLRYAGGGNEQSFRVDLRTLLRYA (DS-A85). The data are shown in Table 1, where the numbers indicate percent internalized receptor.

TABLE 1

| Time (min) | IR | mIR | IR + DS-A85 | mIR + DS-A85 | IR + pepIR | mIR + pepIR |
|---|---|---|---|---|---|---|
| 5 | 6 ± 4 | 4 ± 5 | 5 ± 4 | −1 ± 5 | 6 ± 4 | 5 ± 4 |
| 15 | 39 ± 7 | 2 ± 2 | 9 ± 6 | 0 ± 3 | 2 ± 2 | −2 ± 1 |
| 30 | 68 ± 6 | 4 ± 5 | 14 ± 6 | 2 ± 3 | 6 ± 4 | 0 ± 2 |
| 60 | 74 ± 8 | 5 ± 4 | 17 ± 3 | 1 ± 4 | 2 ± 4 | 2 ± 3 |

Each data point is the mean ± standard error of the mean for 4 experiments, each experiment was done with triplicate samples.

The data show that the mutated insulin receptor mIR does not internalize upon insulin binding, whereas more than 50% of the wild type IR is internalized within 30 minutes. The pepIR peptide inhibits receptor internalization to the same extent as DS-A85.

Effect of peptides on glucose uptake. At maximal insulin stimulation, the addition of pepIR did not significantly affect glucose uptake, indicating that pepIR does not affect GLUT4 internalization. Glucose uptake is enhanced 14±3 fold by the addition of 10 nM insulin. Insulin+10 $\mu$M of the DS-A85 peptide enhances glucose uptake 22±4 fold, whereas addition of insulin+10 $\mu$M pepIR enhances glucose uptake 12±4 fold, a result not significantly different from insulin alone.

The GLUT4pep (SEQ ID NO:2), at a concentration of 10 $\mu$M, does not affect insulin receptor internalization by the transfected cells. In the presence of peptide the per cent internalized receptor is 69±9, in the absence of peptide it is 64±7. The peptide does inhibit the internalization of GLUT4, as shown by the effect on glucose uptake at maximal insulin stimulation. In the presence of 10 nM insulin, the enhancement of glucose uptake was 12±4 fold. The enhancement was increased to 24±2 fold with the addition of the GLUT4pep. The peptide therefore seems to inhibit internalization of GLUT4, but not insulin receptor.

It is evident from the above results that oligopeptides having the sequence of the extracellular domain of a cell surface receptor, and having sequence identity with a region of an MHC class I antigen, are effective in inhibiting the internalization of the corresponding receptor. The peptides are therapeutically useful in enhancing the cellular response to hormones such as insulin.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for inhibiting internalization of an internalizing hormone binding cell surface receptor of a mammalian cell, said method comprising:

contacting said mammalian cell with an effective amount of an oligopeptide of from 8 to 40 amino acids having a sequence other than SEQ ID NO:1 with at least 30% sequence identity with SEQ ID NO:1 as determined by the Wisconsin Package, version 8.0-OpenVMS, Genetics Computer Group, default parameters, and differing by not more than 3 conservative substitutions from an amino acid sequence of an extracellular domain of said cell surface receptor;

wherein said internalization of said cell surface receptor is inhibited.

2. A method according to claim 1, wherein said cell surface receptor is the human insulin receptor.

3. A method according to claim 2, wherein said oligopeptide has the sequence of SEQ ID NO:3 or a fragment thereof.

4. A method according to claim 1, wherein said cell surface receptor is the human insulin sensitive glucose transporter (GLUT 4).

5. A method according to claim 4, wherein said oligopeptide has the sequence of SEQ ID NO:2 or a fragment thereof.

6. A method for inhibiting internalization of an internalizing hormone binding cell surface receptor of a mammalian cell, said method comprising:

contacting said mammalian cell with an effective amount of an oligopeptide of from 8 to 40 amino acids having a sequence other than SEQ ID NO:1 with at least 30% sequence identity with SEQ ID NO:1 as determined by the Wisconsin Package, version 8.0-OpenVMS, Genetics Computer Group, default parameters, and identical to an amino acid sequence of an extracellular domain of said cell surface receptor;

wherein said internalization of said cell surface receptor is inhibited.

* * * * *

```
                         SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
         (A) LENGTH: 23 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:1:

Glu Arg Glu Thr Gln Ile Ala Lys Gly Asn Glu Gln Ser Phe Arg Val
     1               5                  10                  15

Asp Leu Arg Thr Leu Leu Arg
                 20

(2) INFORMATION FOR SEQ ID NO:2:

(i) SEQUENCE CHARACTERISTICS:
         (A) LENGTH: 23 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:2:

Thr Trp Leu Gly Arg Gln Gly Pro Glu Gly Pro Ser Ser Ile Pro Pro
     1               5                  10                  15

Gly Thr Leu Thr Thr Leu Trp
                 20

(2) INFORMATION FOR SEQ ID NO:3:

(i) SEQUENCE CHARACTERISTICS:
         (A) LENGTH: 24 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:3:

Lys Thr Asp Ser Gln Ile Leu Lys Glu Leu Glu Glu Ser Ser Phe Arg
     1               5                  10                  15

Lys Thr Phe Glu Asp Tyr Leu His
                 20

(2) INFORMATION FOR SEQ ID NO:4:

(i) SEQUENCE CHARACTERISTICS:
         (A) LENGTH: 27 amino acids
         (B) TYPE: amino acid
```

-continued

```
        (C) STRANDEDNESS: single
        (D) TOPOLOGY: linear (ii) MOLECULE TYPE: peptide (xi) SEQUENCE DESCRIPTION: SEQ ID NO:4:

Pro Lys Thr Asp Ser Gln Ile Leu Lys Glu Leu Glu Ser Ser Phe
    1               5                   10                  15

Arg Lys Thr Phe Glu Asp Tyr Leu His Asn Val
                20                  25

(2) INFORMATION FOR SEQ ID NO:5:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Gly Asn Glu Gln Ser Phe Arg Val Asp Leu Arg Thr Leu Leu Arg Tyr
    1               5                   10                  15

Ala Gly Gly Gly Asn Glu Gln Ser Phe Arg Val Asp Leu Arg Thr Leu
                20                  25                  30

Leu Arg Tyr Ala
                35
```